United States Patent [19]

Schatz et al.

[11] 4,204,998

[45] May 27, 1980

[54] N-AMINO INDOLE DERIVATIVES HAVING PHARMACOLOGICAL ACTIVITY

[75] Inventors: Franz Schatz, Maria-Enzersdorf Südstadt; Christian Stammbach, Zofingen; Kurt Thiele, Zofingen; Theodor W. Wagner-Jauregg, Zofingen; Ludwig Zirngibl, Zofingen; Johanna Fischer, Reiden; Ulrich Jahn, Zofingen, all of Switzerland

[73] Assignee: Siegfried Aktiengesellschaft, Zofingen, Switzerland

[21] Appl. No.: 903,128

[22] Filed: May 5, 1978

Related U.S. Application Data

[63] Continuation of Ser. No. 813,856, Jul. 8, 1977, abandoned, which is a continuation of Ser. No. 565,739, Mar. 31, 1975, abandoned.

[30] Foreign Application Priority Data

Mar. 29, 1974 [CH] Switzerland .................... 4339/74

[51] Int. Cl.² .............. C07D 209/44; C07D 209/08; C07D 249/18; C07D 235/22

[52] U.S. Cl. .............. 260/326.15; 260/326.1; 260/326.13 D; 424/269; 424/273 R; 424/273 B; 424/273 N; 424/274; 546/273; 548/257; 548/260; 548/329; 548/371

[58] Field of Search ...................... 260/326.15

[56] References Cited

PUBLICATIONS

Meyer, J. Chem. Soc. 1965, 3451-3454.
Arguzov, J. Gen. Chem. USSR (1957) 9, 2341-2354.
Schatz et al., Chem. Abs. 84, 30886 (1975).
Jones, J.C.S. Perkins I, 2728-2731 (1972).
Somei et al., I. Tet Letters 461-462 (1974).
Somei et al. II Tet Letters 3605-3608 (1974).

*Primary Examiner*—Mark L. Berch
*Attorney, Agent, or Firm*—Finnegan, Henderson, Farabow, Garrett & Dunner

[57] ABSTRACT

Novel hydrazines are disclosed in which one of the nitrogen atoms forms a ring member of the five membered ring of a [4.3.0] heterobicyclic compound which may be substituted elsewhere in the ring system. Characteristic ring systems described include indole and benztriazole ring systems. The compounds possess antidepressant properties as well as anti-microbial, in particular fungistatic and bacteriostatic, properties.

8 Claims, No Drawings

N-AMINO INDOLE DERIVATIVES HAVING PHARMACOLOGICAL ACTIVITY

This application is a continuation of Application Ser. No. 813,856, filed July 8, 1977, which is a continuation of Application Ser. No. 565,739, filed Mar. 31, 1975, both of which are abandoned.

This invention relates to new hydrazines, to a process for the production thereof and to pharmaceutical compositions comprising the same.

Relatively few chemical compounds have hitherto been described which consist of a six-membered ring having fused thereto a five-membered ring containing at least one ring nitrogen atom and comprising a secondary or tertiary amino group bonded to a ring nitrogen atom. Such systems can be considered to be hydrazines in which one of the nitrogen atoms forms a ring member of the five-membered ring of a [4.3.0] heterobicyclic compound. Compounds of this type which have hitherto been characterised include 1-dimethylamino-3-phenyl-indole and 1-phenyl-amino-3-phenyl-indole, as well as their 5-chloro analogues. Reference is made in this connection to F. Troxler, in Indoles, Part II, pages 191–192, edited by W. J. Houlihan, Wiley-Interscience, New York-London, 1972, and to R. J. Sundberg, The Chemistry of Indoles, page 397, Academic Press, New York-London, 1970. The aforesaid compounds have been produced by procedures specific to individual compounds and not applicable to the production of structurally related compounds.

According to one aspect of the present invention, there is provided a compound having the general formula:

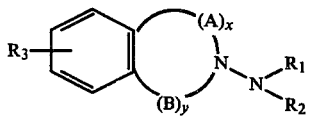

I wherein A and B are nitrogen or carbon atoms having any remaining valencies not utilised in ring formation occupied by hydrogen in the case of nitrogen and carbon or by inert substituents in the case of carbon, x and y are 0, 1 or 2 such that $x+y=2$, $R_1$ is hydrogen or an organic group and $R_2$ is an organic group such that at least one of $R_1$ and $R_2$ contains at least two carbon atoms which do not form part of a benzene ring, $R_3$ is an inert substituent, and pharmaceutically acceptable salts thereof.

According to a further aspect of the present invention there is provided a process for the production of a compound having the general formula:

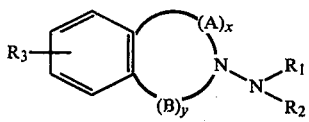

I wherein A, B, x, y, $R_1$ to $R_3$ are as defined above, which comprises reacting a compound having the general formula:

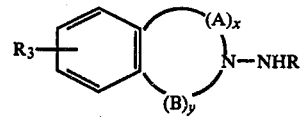

II wherein R is a hydrogen atom or an organic group with a compound of formula R'X in which R' contains at least two carbon atoms which do not form part of a benzene ring and X is a radical which is split off in a reaction wherein a $>N-R'$ bond is formed and combined with a hydrogen atom split off from the nitrogen atom.

With the compounds according to the invention, a hydrazine moiety forms part of a heterobicyclic ring system exemplified, in particular by the indole (III), isoindole (IV), indazole (V), isoindazole (VI), 1,3-benzisodiazole (VII) and benztriazole (VIII) ring structures which are as follows:

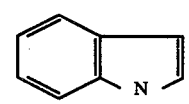

III

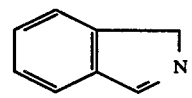

IV

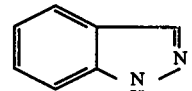

V

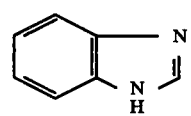

VI

VII

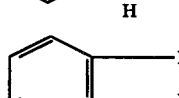

VIII

The basic heterobicyclic ring system can comprise various substituents on the five-membered ring system and/or the six-membered ring system and the novel compounds have been found to possess anti-microbial properties, in particular fungistatic and bacteriostatic properties, which render them suitable for use for chemotherapeutic purposes, and additionally possess pharmacodynamic effects in a number of respects. Thus the compounds possess anti-depressant properties, this being the case to a conspicuous degree with the compound 1-[N-methyl-N(2'-dimethylaminoethyl)-amino]-3-phenyl-indole hydrochloride. The compounds of this invention are rendered particularly suitable for use in pharmaceutical compositions by their remarkably low toxicity.

In general, the compounds according to this invention which have particularly valuable anti-microbial properties and/or pharmacodynamic effects are derivatives of 1-amino-3-phenyl-indole and of 1-amino-benztriazole. With compounds of the present invention, and with these preferred ring systems, in particular, particularly promising results have been obtained when the amino group is either substituted by an acyl group, for example a benzyl group or an alkanoyl group containing up to 4 carbon atoms, for example an acetyl or propionyl group or by one or two alkyl groups preferably containing from 2 to 5 carbon atoms. The aforesaid properties of the compounds are further intensified if in such a case an acyl group or an alkyl group, preferably a pair of alkyl groups are in turn substituted by a tertiary amino group which is preferably a dialkylamino group whose alkyl radicals contain up to 3 carbon atoms. Furthermore, it is preferably for the heterobicyclic structure and the phenyl group of the aforesaid 1-amino-3-phenyl-indole structure, to be substituted by a halogen or an alkyl group containing up to 16 carbon atoms or a cycloalkyl group.

When preparing the aforesaid preferred types of compound according to this invention the radical R' in the compound R'X will thus be an acyl radical and can be a benzoyl radical provided that it is substituted on the benzene nucleus by at least one carbon-containing group. R' can also be an alkyl group or an aralkyl group which, in their turn, can be substituted, for example by halogen, hydroxyl groups which may be esterified, carboxyl groups which may be esterified, primary, secondary or tertiary amino groups, which can form part of heterocyclic ring systems, nitro, cyano, thiocyano, cyanato, thiocyanato and isothiocyanato groups. Although the aforesaid preferred tertiary amino substituent may be present in the group R' from the outset, it can be introduced into the group $R_1$ or $R_2$ in the reaction product by substitution of for example a halogen atom or a phenolic hydroxyl group introduced thereinto in the group R'.

The radical X which combines with hydrogen in the reaction whereby the compounds of the present invention are formed is preferably a chlorine atom, a bromine atom or an alkoxy group, in particular a methoxy or an ethoxy group.

The starting compound of general formula II which is employed in the process of this invention is preferably one in which R is either hydrogen or a methyl group. A primary amino group can be incorporated in the starting compound during the formation of the nitrogen-containing ring system. Thus, a dihydrocinnoline can be boiled with a dilute mineral acid at 100° C. to give a 1-amino indole. A 1-methylamino-3-methyl indole has been produced by boiling 1-formamido-3-methyl indole with formic acid.

The heterobicyclic structure of the hydrazine used as starting material can, as already indicated above, be substituted at one or more of a number of positions, for example by halogen, alkyl, alkoxy, substituted alkyl, substituted alkoxy of phenyl groups.

The products obtained by the aforesaid process of this invention can be converted into the form of acid addition salts by reaction with an inorganic acid, for example hydrochloric acid, or an organic acid, for example an organically substituted sulphonic acid, for example cyclohexyl sulphonic acid. Depending upon the nature of substituents in the product, it may even be possible to isolate the product in the form of a salt with a base. The physical form of the product of the aforesaid reaction may indeed by such that it cannot be readily isolated in other than salt form. The novel compounds of this invention can also be converted into quaternary ammonium salts.

It will be appreciated that for therapeutic use, the compounds of this invention can be made up, in accordance with well known pharmaceutical techniques, into compositions having as an essential active ingredient the compound of the invention in association with a pharmaceutical carrier therefor. If desired, the compositions can be made up in a dosage unit form suitable for the particular mode of administration, the quantity of active ingredient in each dosage unit being such that one or more units are required for each therapeutic administration. The dosage unit may exist, for example, in the form of a tablet, pill, sachet, packaged powder or encapsulated powder for oral administration or in the form of a sterile injectable solution or suspension, if desired contained in an ampoule, for parenteral administration.

The following Examples illustrate the invention:

EXAMPLE 1

1-[bis-(2'-diethylaminoethyl)]-amino-3-phenyl-indole hydrochloride 23.4 G of sodium amide (50%) in toluene (0.3 mol) were added dropwise and while stirring to a suspension of 20.8 g (0.1 mol) of 1-amino-3-phenyl-indole in 200 ml of toluene. The temperature of the suspension rose to about 40° C., and the mixture became a light brown in colour. A solution of 30 g (0.22 mol) of diethylaminoethyl chloride in 250 ml of toluene was then added dropwise to the warm reaction mixture which was then heated for 3 hours under reflux. The reaction mixture initially darkened but subsequently developed a light yellow colouring.

The reaction mixture was then cooled and the reaction product was extracted three times with, on each occasion, 150 ml of 2 N acetic acid. The aqueous phases obtained were each washed once with ether, made alkaline with 2 N-sodium carbonate solution and extracted with ether. The combined ether extracts were dried and concentrated. The resulting oil was supplied with benzene to a 300 ml Alox Woelm column and eluted. The reaction product, purified in this way and constituted by 31 g of light brown oil was taken up in anhydrous ether and ethereal hydrogen chloride was added thereto while stirring until no more hydrochloride was precipitated. The precipitate was filtered off, washed with ether and dried. A yield of hydrochloride of 26.0 g (55% of the theoretical) was obtained. The hydrochloride had a melting point of 233°–235° C. Analysis of this product was as follows:

$C_{26}H_{38}N_4.2$ HCl (479.55): Calculated: C 65.12, H 8.41, N 11.68, Cl 14.78: Found: C 65.14, H 8.39, N 11.67, Cl 14.53.

EXAMPLE 2

1-[N-methyl-N-(3'-dimethylamino)-propyl]-amino-3-phenyl-indole hydrochloride

A suspension of 5.4 g of sodium amide (50%) in toluene, followed by a solution of 6.5 g (0.05 mol) of 3-dimethylaminopropyl chloride in 50 ml of toluene, were added dropwise to a solution of 11.1 g (0.05 mol) of 1-methylamino-3-phenyl-indole in 150 ml of anhydrous toluene, while stirring vigorously. The mixture obtained was then heated under reflux for 3 hours. The reaction mixture was cooled and extracted three times, each time with 150 ml of 2 N acetic acid. The acetic acid extracts were made alkaline with ammonia and combined. The crude product thus obtained, existing partially as an oil, was dissolved in ethyl acetate. The solution was washed with water, dried and concentrated. The oil thus obtained was purified by chromatography using a short column of Alox Akt. II and was eluted with ether. The hydrochloride of the reaction product was precipitated from the ethereal solution by adding ether/HCl and was filtered off and dried. The melting point of the hydrochloride was 183°–185° C. and the yield of hydrochloride was about 80% of theoretical.

Analytical data: $C_{20}H_{26}N_3Cl$ (343.9): Calculated in atoms: $C_{20}H_{26}N_3$-10.31% Cl: Found: $C_{19.6}H_{25.7}N_3$-11.15% Cl.

The 1-methylamino-3-phenyl-indole starting material has not hitherto been described and may be prepared by the following method:

25 G (0.1 mol) of 1-acetylamino-3-phenyl-indole (which can be obtained with a good yield from 1,4-dihydro-4-phenyl cinnoline in 5% acetic acid), 48 g (0.2 mol) of the methyl ester of p-toluene sulphonic acid and 12.8 g (0.2 mol) of finely powdered potassium hydroxide were suspended in 150 ml of toluene and heated for 4 hours under reflux. After cooling, the reaction product was poured into water. The organic phase was separated out, dried over sodium sulphate and concentrated. 31 G of a crude oil comprising 1-(N-methyl-N-acetylamino)-3-phenyl-indole were obtained. The oil was purified using an Alox Akt. II column with benzene and the reaction product was dissolved in 610 ml of ethanol and 210 ml of hydrochloric acid and heated for 2 hours under reflux. The reaction mixture was then poured onto ice and made alkaline with ammonia, the reaction product precipitating as a white, crystalline precipitate. Filtering, drying and recrystallisation of the reaction product from ethanol/water yielded 1-methylamino-3-phenyl-indole of melting point 60°–62° C. (yield 60%, based on the dihydrophenyl cinnoline original starting material).

Analysis: $C_{15}H_{14}N_2$ (222.0): Found in atoms: $C_{15}H_{13.9}N_2$.

EXAMPLE 3

1-(p-acetaminobenzene sulphonylamino)-3-phenyl-indole 11.7 G (0.05 mol) of p-acetaminobenzene sulphonyl chloride were added in portions and with stirring to a solution of 15.6 g (0.075 mol) of 1-amino-3-phenyl-indole in 100 ml of pyridine. The temperature of the mixture rose to about 45° C. The mixture was then heated to 60° C. and stirred for 3 hours at this temperature. The red solution obtained was then concentrated by evaporation under vacuum. The viscous, oily residue which was obtained was taken up in a mixture of benzene and chloroform (1:1 by volume) and chromatographically purified through a column of 300 ml Alox Woelm neutral Akt. II. The resulting oily product was crystallised from a little ethanol and was recrystallised from ethanol/water. The crystals of 1-(p-acetaminobenzene sulphonylamino)-3-phenyl-indole melted at 190°–193° C. and were obtained in a yield of 16.5 g (55% of the theoretical).

Analysis: $C_{22}H_{19}N_3O_3S$ (332.5): Found in atoms: $C_{21.8}H_{18.7}N_3$.

1-(p-aminobenzene sulphonylamino)-3-phenyl-indole melting at 176°–177° C. could be obtained from this product by deacetylation.

EXAMPLE 4

1-(3'-dimethylaminopropionylamino)-3-phenyl-indole 4.75 G (0.028 mol) of β-bromopropionic acid chloride in 10 ml of toluene and 2.55 g (0.025 mol) of triethylamine in 10 ml of toluene were added dropwise and while stirring to a solution of 5 g (0.025 mol) of 1-amino-3-phenyl-indole in 80 ml of anhydrous tetrahydrofuran. The temperature of the solution rose to about 55° C. Stirring of the reaction mixture thus obtained was then effected for 1 hour without application of heat and for 1 hour while heating it at 60° C. The triethylamine hydrochloride which precipitated was then removed by filtration and the clear light brown filtrate was completely concentrated by evaporation in a rotary evaporator and the residue was recrystallised from ethanol. 1-(3'-bromopropionylamino)-3-phenyl-indole which was obtained as an intermediate product in a yield of 6.3 g (77% of theoretical), melted at 185°–186° C.

5 G (0.015 mol) of this intermediate product were suspended in 50 ml of anhydrous dioxane and a mixture of 10 ml of chilled tetrahydrofuran and 1.8 g (0.04 mol) of dimethylamine was added thereto. The entire reaction mixture was kept at 40° C. in a glass autoclave for 16 hours while stirring. The dimethylamine hydrobromide which separated out was then removed and the solution which remained was concentrated by evaporation and the residue obtained was recrystallised from ethanol. 3.85 G (86% of the theoretical) of 1-(3'-dimethylaminopropionyl)-3-phenyl-indole of melting point 137°–138° C. were obtained.

Analytical data: $C_{19}H_{21}N_3O$ (307.4): Calculated: C 74.23, H 6.89, N 13.67: Found: C 74.13, H 6.84, N 13.83.

EXAMPLE 5a 1-(3'-dimethylaminopropionylamino)-5-methyl benztriazole cyclohexylamine sulphonate A solution of 14.8 g (0.1 mol of 1-amino-5-methyl benztriazole in 200 ml of anhydrous benzene was placed under a nitrogen atmosphere and, over a period of 30 minutes, a solution of 18.9 g (0.11 mol) of β-bromopropionyl chloride in 25 ml of anhydrous benzene and 10.1 g (0.10 mol) of triethylamine were simultaneously added to the solution while stirring the latter. The addition was so made that the amount of acid chloride added was always greater than the amount of amine. The temperature of the mixture rose to above 40° C. Stirring was then continued for 1 hour without application of heat and was continued for a further hour with heating to 60° C. following by stirring for two further hours without application of heat. The organic phase was then poured off from a greasy deposit in the reaction vessel and was washed with water. The deposit was taken up in chloroform and was also washed with water. The organic phases obtained were dried over sodium sulphate, combined and completely concentrated by evaporation. 24 G of the intermediate product, 1-(β-bromopropionylamino)-5-methyl benztriazole were obtained as residue in the form of a frothy resin.

The intermediate product was dissolved without further purification in 150 ml of anhydrous dioxane. Without applying heat to the solution obtained a solution of 7.5 g (0.167 mol) of dimethylamine in 50 ml of anhydrous dioxane was added dropwise thereto over a period of 45 minutes. The internal temperature of the contents of the reaction vessel rose to more than 40° C. Stirring was then effected for another two hours while keeping the reaction mixture at 50° C. and finally for 2½ hours without application of heat. After filtering off the precipitated dimethylamine hydrobromide and concentrating the filtrate by evaporation, there were obtained 26 g of a viscous resin, which was added to chloroform and filtered through a column of 250 ml Alox Woelm Akt. II. After evaporation of the filtrate, 20 g of a viscous, light brown oil were obtained which was dissolved in alcohol/ether and precipitated therefrom as a cyclohexylamine sulphonate salt of melting point 133°–136° C. addition of cyclohexylaminesulphonic acid.

Analytical data: $C_{12}H_{17}N_5O \cdot C_6H_{13}NSO_3$ (426.6): Calculated: O 15.0, S 7.52: Found: O 14.8, S 7.48: Found in atoms: $C_{18.1}H_{29.9}N_{6.00}$.

EXAMPLE 5b

In an alternative procedure for obtaining the product of Example 5a, 0.74 g (5 m.mol) of 1-amino-5-methyl benztriazole were dissolved in 15 ml of anhydrous benzene. 0.3 G (5.5 m.mol) of sodium methylate and then 0.66 g (5 m.mol) of 3-dimethylaminopropionic acid ethyl ester were added to the benzene solution which was then heated for 3 hours to reflux temperature. A further 0.2 g of sodium methylate was then added and boiling was effected for another 4 hours under reflux. The reaction mixture was then shaken with 5 ml of 10% hydrochloric acid and the aqueous phase was made alkaline and extracted with chloroform. The chloroform extract was dried over sodium sulphate and concentrated by evaporation. The oily residue (0.88 g) thus obtained was dissolved in ethanol and an alcoholic solution of 0.57 g (3.2 m.mol) of cyclohexylamine-sulphonic acid was added. The salt which precipitated was recrystallised from ethanol and found to have a melting point of 136°–138° C. The salt produced no depression of mixed melting point, unlike the product which had been obtained in Example 5a.

EXAMPLE 5c

The hydrochloride of 1-(3'-dimethylaminopropionylamino)-5-methyl benztriazole was obtained by concentrating by evaporation the chloroform eluate of the column chromatography carried out in Example 5a. The residue was dissolved in ether and treated with an ethereal HCl solution. The salt which thus precipitated had a melting point about 170° C. which dropped to 163°–166° C. after recrystallisation of the salt from chloroform/ethyl acetate.

Analytical data: $C_{12}H_{17}N_5O \cdot HCl$ (283.8): Calculated: Cl 12.49: Found: Cl 12.24.

EXAMPLE 6

1-diethylaminoacetylamino benztriazole

Using a similar procedure to that of Example 5a, 1-amino benztriazole was allowed to react with bromacetyl chloride and the crude bromacetyl derivative obtained in a yield of 75% of the theoretical was then reacted with diethylamine. The crude reaction product then obtained was purified chromatographically, as in Example 5a. The free base, 1-diethylaminoacetylaminobenztriazole, recrystallised from benzene, melted at 115°–116° C. To obtain the hydrochloride of the free base, the latter was dissolved in ethereal hydrogen chloride and recrystallised from ethanol. The hydrochloride melted at 185°–188° C.

Analytical data: $C_{12}H_{17}N_5O \cdot HCl$ (283.8): Calculated: C 50.79, H6.39, N 24.69, O 5.64, Cl 12.49: Found: C 50.76, H 6.66, N 25.53, O 5.27, Cl 13.13.

EXAMPLE 7

1-[bis-(2'-diethylaminoethyl)]amino-benztriazole 17.5 G of a 50% suspension of sodium amide in toluene were added to a suspension of 9.6 g (0.072 mol) of 1-aminobenztriazole in 150 ml of anhydrous toluene. 21.8 G (0.161 mol) of diethylaminoethyl chloride were then added dropwise at room temperature. Heating of the reaction mixture under reflux for 3 hours was then effected. Initially a solid precipitate formed, but this subsequently dissolved.

The reaction mixture was then cooled and extracted three times, each time with 150 ml of 2 N-acetic acid. The combined aqueous phases were twice extracted in reverse, each time with 50 ml of ether, and then excess ammonia was added. Extraction with ether was then effected again. The ethereal extract obtained was concentrated by evaporation to yield 24.3 g of an oil, which, after chromatographic purification in analogous manner to Example 5a, concentration by evaporation and distillation, yielded 18.3 g of 1-[bis-(2'-diethylaminoethyl)]amino benztriazole of boiling point 140°–145° C./0.001 mm.Hg. $n_D^{20}$ 1.5172. Yield 77% of the theoretical.

Analytical data: $C_{18}H_{32}N_6$ (332.6): Found in atoms: $C_{18.05}H_{32.1}N_{6.00}$.

EXAMPLE 8

1-[N-methyl-N-(2'-dimethylamino)-ethyl]-aminobenztriazole hydrochloride

Example 7 was repeated using 1-methylaminobenztriazole and dimethylaminoethyl chloride in place of 1-aminobenztriazole and diethylaminoethyl chloride. The free base was obtained as an oil of boiling point 102°–105° C./0.01 mm.Hg, in a yield of 77% of theoretical; $n_D^{20}$ 1.5403. The hydrochloride obtained by means of HCl/ether melted at 187°–190° C.

Analytical data for hydrochloride: $C_{11}H_{17}N_5 \cdot HCl$ (255.8): Calculated: Cl 13.86: Found: Cl 14.10: Found in atoms: $C_{11.3}H_{18}N_{5.00}$.

Additional examples of compounds according to the present invention which have been prepared, are:

| | |
|---|---|
| 1. 1-(3'-Carboxypropionylamino)-3-phenyl-indole | M.p. 189°–190° C. |
| 2. 1-(α-Chlornicotinoyl-amino)-3-phenyl-indole | M.p. 169°–170° C. |
| 3. 1-(p-Nitrobenzoylamino)-3-phenyl-5-chlor-indole | M.p. 233°–241° C. |
| 4. 1-(o-Chloro-p-nitrobenzoylamino)-3-phenyl-indole | M.p. 187°–189° C. |
| 5. 1-(o-Chloro-p-aminobenzoylamino)-3-phenyl-indole | M.p. 189°–190° C. |
| 6. 1-(3'-Dimethylaminopropionylamino)-benztriazole-cyclohexyl sulphonate semihydrate | M.p. 101°–103° C. |
| 7. 1-[N-Methyl-N-(2'-dimethylaminoethyl)-amino]-3-phenyl-indole hydrochloride | M.p. 188°–190° C. |
| 8. 1-[N-Methyl-N-(2'-diethylaminoethyl)-amino]-3-phenyl-indole hydrochloride | M.p. 140°–143° C. |
| 9. 1-[N-Methyl-N-(3'-dimethylaminopropyl)-amino]-3-phenyl-5-chloro-indole hydrochloride | M.p. 184°–186° C. |
| 10. 1-[N-Methyl-N-(2'-dimethylaminoethyl)-amino]-3-phenyl-5-methyl-indole | B.p. 165°–170° C. |

| | | |
|---|---|---|
| -continued | | |
| 11. 1-[N-Methyl-N-(2'-dimethylaminoethyl)-amino]-3-(4'-methoxyphenyl)-indole | B.p. 215°–200° C. 0.01 | |
| 12. 1-[N-Methyl-N-(3'-dimethylaminopropyl)-amino]-3-p-tolyl-5-chloro-indole hydrochloride | M.p. 205°–207° C. | |
| 13. 1-[N-Methyl-N-(3'-dimethylaminopropyl)-amino]-3-(p-chlorophenyl)-5-chloro-indole hydrochloride | M.p. 209°–210° C. | |
| 14. 1-[N-Methyl-N-(2'-diethylaminoethyl)-amino]-3-phenyl-5-fluo-indole hydrochloride | M.p. 117°–118° C. | |
| 15. 1-[N-Methyl-N-(3'-dimethylaminopropyl)-amino]-3-phenyl-5-bromo-indole hydrochloride | M.p. 152°–156° C. | |
| 16. 1-[N-Methyl-N-(2'-diethylaminoethyl)-amino]-benztriazole | B.p. 113°–115° C. 0.01 | |
| 17. 1-[N-Methyl-N-(3'-dimethylaminopropyl)-amino]-benztriazole hydrochloride | M.p. 135°–138° C. | |
| 18. 1-[N-Methyl-N-(2'-dimethylaminoethyl)-amino]-5-methyl-benztriazole hydrochloride | M.p. 189°–191° C. | |
| 19. 1-[N-Methyl-N-(3'-dimethylaminopropyl)-amino]-5-methyl-benztriazole hydrochloride | M.p. 202°–205° C. | |
| 20. 1-[bis-(2'-Diethylaminoethyl)]-amino-3-phenyl-indole-di-methiodide | (amorphous) | |
| 21. 1-[bis-(3'-Dimethylaminopropyl)]-amino-3-phenyl-5-chloro-indole dihydrochloride | M.p. 257° C. | |
| 22. 1-[bis-(2'-Dimethylaminoethyl)]-amino-3-phenyl-5-fluo-indole dihydrochloride | M.p. 240° C. | |
| 23. 1-[bis-(2'-Diethylaminoethyl)]-amino-3-phenyl-5-bromo-indole dihydrochloride | M.p. 90°–95° C. | |
| 24. 1-[bis-(2'-Dimethylaminoethyl)]-amino-3-phenyl-5-methyl-indole dihydrochloride | M.p. 245°–247° C. | |
| 25. 1-[bis-(2'-Dimethylaminoethyl)]-amino-3-(p-chlorphenyl)-5-chloro-indole dihydrochloride | M.p. 246°–250° C. | |
| 26. 1-[bis-(2'-Diethylaminoethyl)]-amino-3-(p-chlorphenyl)-5-chloro-indole dihydrochloride semihydrate | M.p. 245° C. | |
| 27. 1-[bis-(3'-Dimethylaminopropyl)]-amino-3-(p-chlorphenyl)-5-chloro-indole dihydrochloride | M.p. 278°–279° C. | |
| 28. 1-[bis-(2'-Dimethylaminoethyl)]-amino-3-(p-chlorophenyl)-5-fluo-indole dihyrochloride | M.p. 270°–271° C. | |
| 29. 1-[bis-(2'-Diethylaminoethy)]-amino-3-(p-chlorphenyl)-5-fluo-indole dihydrochloride | M.p. 50° C. | |
| 30. 1-[bis-(3'-Dimethylaminopropyl)]-amino-3-(p-chlorphenyl)-5-fluo-indole dihydrochloride | M.p. 275° C. | |
| 31. 1-[bis-(2'-Dimethylaminoethyl)]-amino-benztriazole dicyclohexyl sulphonate | M.p. 85°–87° C. (decomp.) | |
| 32. 1-[bis-(3'-Dimethylaminopropyl)]-amino-benztriazole dicyclohexyl sulphonate. | M.p. 136°–138° C. (decomp.) | |

We claim:

1. A compound of the formula:

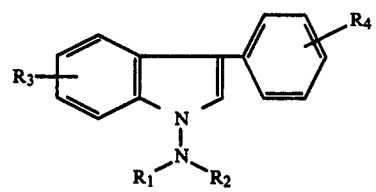

wherein:
$R_1$ is $C_1$–$C_3$ dialkylamino-$C_2$–$C_5$ alkyl;
$R_2$ is selected from the group consisting of hydrogen, $C_1$–$C_3$ alkyl and $C_1$–$C_3$ dialkylamino-$C_2$–$C_5$ alkyl;
$R_3$ is selected from the group consisting of hydrogen, halogen and methyl; and
$R_4$ is selected from the group consisting of hydrogen, methyl, methoxy and chloro
and pharmaceutically acceptable salts of such compounds.

2. The compound of claim 1, which is 1-[N-methyl-N-(2'-dimethylaminoethyl)-amino]-3-phenyl indole or a pharmacologically acceptable salt thereof.

3. The compound of claim 2, which is 1-[N-methyl-N-(2'-dimethylaminoethyl)-amino]-3-phenyl indole hydrochloride.

4. The compound of claim 1, which is 1-[N-methyl-N-(3'-dimethylaminopropyl)-amino]-3-phenyl indole or a pharmacologically acceptable salt thereof.

5. A compound of claim 1, wherein $R_2$ is methyl.

6. A compound of claim 1, wherein said dialkylamino alkyl radical of $R_1$ and $R_2$ is $C_1$–$C_3$ dialkylamino-$C_2$–$C_3$ alkyl.

7. The compound of claim 1, which is 1-[N-methyl-N-(2'-diethylaminoethyl)-amino]-3-phenyl indole or a pharmacologically acceptable salt thereof.

8. The compound of claim 1, which is 1-[N-methyl-N-(2'-dimethylaminoethyl)-amino]-3-(4'-methoxyphenyl)-indole or a pharmacologically acceptable salt thereof.

* * * * *

UNITED STATES PATENT AND TRADEMARK OFFICE
CERTIFICATE OF CORRECTION

PATENT NO. : 4,204,998
DATED : May 27, 1980
INVENTOR(S) : Franz Schatz et al.

It is certified that error appears in the above-identified patent and that said Letters Patent are hereby corrected as shown below:

TITLE: Should read "INDOLE DERIVATIVES HAVING PHARMACOLOGICAL ACTIVITY"

rather than "N-AMINO INDOLE DERIVATIVES HAVING PHARMACOLOGICAL ACTIVITY"

Signed and Sealed this

Twenty-sixth Day of August 1980

[SEAL]

*Attest:*

SIDNEY A. DIAMOND

*Attesting Officer*   *Commissioner of Patents and Trademarks*